(12) United States Patent
Baid (10) Patent No.: US 9,636,484 B2
(45) Date of Patent: May 2, 2017

(54) CATHETER APPARATUS

(71) Applicant: POLY MEDICURE LIMITED, Faridabad, Haryana (IN)

(72) Inventor: Rishi Baid, New Delhi (IN)

(73) Assignee: POLY MEDICURE LIMITED, Haryana (IN)

(*) Notice: Subject to any disclaimer, the term of this patent is extended or adjusted under 35 U.S.C. 154(b) by 237 days.

(21) Appl. No.: 14/380,358

(22) PCT Filed: Feb. 13, 2013

(86) PCT No.: PCT/IB2013/051158
§ 371 (c)(1),
(2) Date: Aug. 21, 2014

(87) PCT Pub. No.: WO2013/124765
PCT Pub. Date: Aug. 29, 2013

(65) Prior Publication Data
US 2015/0328438 A1    Nov. 19, 2015

(30) Foreign Application Priority Data

Feb. 21, 2012    (IN) .......................... 486/DELI/2012

(51) Int. Cl.
*A61M 25/06*    (2006.01)
*A61M 5/162*    (2006.01)

(52) U.S. Cl.
CPC .... *A61M 25/0631* (2013.01); *A61M 25/0606* (2013.01); *A61M 25/0618* (2013.01); *A61M 5/1626* (2013.01); *A61M 2210/12* (2013.01)

(58) Field of Classification Search
CPC .. A61M 5/3243; A61M 5/3273; A61M 25/06; A61M 25/0612; A61M 25/0618;
(Continued)

(56) References Cited

U.S. PATENT DOCUMENTS 5,558,651 A    9/1996    Crawford et al.
7,534,227 B2 *    5/2009    Kulli .................. A61M 5/3273
                                                         604/164.08

(Continued)

FOREIGN PATENT DOCUMENTS

EP    2251057 B1    11/2010
GB    2451153 B    1/2009

(Continued)

OTHER PUBLICATIONS

International Search Report for PCT/IB2013/051158 dated Jun. 5, 2013.

*Primary Examiner* — Imani Hayman
*Assistant Examiner* — James D Ponton
(74) *Attorney, Agent, or Firm* — Moore & Van Allen PLLC; Henry B. Ward, III (57) ABSTRACT

An intravenous catheter apparatus having a needle having a needle shaft, a needle tip at the distal end of the needle shaft and a needle hub mounted to the proximal end of the needle shaft, an intravenous catheter tube mounted to a catheter hub and a needle guard movable on the needle shaft. The needle guard having a base portion having a needle passage extending in an axial direction from a proximal side of the base portion through the base portion to a distal side of the base portion, first and second arms extending substantially in the axial direction from the distal side of the base portion and a distal wall which is transversely arranged at a distal region of the first arm. A recess is provided in the needle guard that receives a stopping element for stopping movement of the needle shaft relative to the needle guard.

23 Claims, 6 Drawing Sheets

(58) Field of Classification Search
CPC ........ A61M 25/0631; A61M 2005/325; A61M 25/0606; A61M 25/0625; A61M 25/0637; A61M 5/1626
See application file for complete search history.

(56) References Cited

U.S. PATENT DOCUMENTS

| | | | | |
|---|---|---|---|---|
| 2005/0277879 | A1* | 12/2005 | Daga | A61M 25/0618 604/110 |
| 2009/0299291 | A1* | 12/2009 | Baid | A61M 5/3273 604/164.08 |
| 2010/0222749 | A1* | 9/2010 | Baid | A61M 5/3273 604/263 |
| 2011/0218496 | A1* | 9/2011 | Bierman | A61M 25/0606 604/164.13 |
| 2012/0277679 | A1* | 11/2012 | Steube | A61M 25/0618 604/164.08 |

FOREIGN PATENT DOCUMENTS

| | | |
|---|---|---|
| WO | WO 2009/010847 A2 | 1/2009 |
| WO | WO 2009/116080 A2 | 9/2009 |
| WO | WO 2011/036574 A1 | 3/2011 |
| WO | WO 2011/138746 A1 | 11/2011 |
| WO | WO 2011/154767 A1 | 12/2011 |
| WO | WO 2012/038899 A1 | 3/2012 |

* cited by examiner

CATHETER APPARATUS

CROSS-REFERENCE TO THE RELATED APPLICATION

This application claims priority from Indian Patent Application No. 486/DEL/2012 dated Feb. 21, 2012, the entire disclosure of which is incorporated herein by reference.

FIELD OF THE INVENTION

The invention relates to a needle guard for use in a medical device, in particular for use in a catheter apparatus. The needle guard includes a base portion having a needle passage extending in an axial direction from a proximal side of the base portion through the base portion to a distal side of the base portion. The needle guard further includes first and second arms extending substantially in the axial direction from the distal side of the base portion and a distal wall which is transversely arranged at a distal region of the first arm.

BACKGROUND OF THE INVENTION

Such needle guards are generally known and are used to cover the tip of a needle of a medical device after use of the medical device. Typically, needle guards are devised to automatically cover the needle tip after withdrawal of the needle, for example, from a patient. The needle guard thereby serves to prevent accidental pricking of, for example, a medical practitioner by the needle tip after removal of the needle from the medical device. Thereby the needle can be safely disposed of after use, without the danger of transmitting possibly highly infectious and/or deadly diseases to the medical practitioner from the patient.

SUMMARY OF THE INVENTION

Generally speaking, the term proximal refers to a region of the device or a location on the device which is closest to, for example, a clinician using the device. In contrast to this, the term distal refers to a region of the device which is farthest from the clinician, for example, the distal region of a needle will be the region of a needle containing the needle tip which is to be inserted e.g. into a patient's vein.

It is an object of the invention to provide an improved needle guard.

This object is satisfied by a needle guard in accordance with the claim 1.

The needle guard of the present invention includes a base portion made of a first material and having a needle passage which extends in an axial direction from a proximal side of the base portion through the base portion to a distal side of the base portion, such that a needle having a principal outer profile can be movably arranged in the needle passage. The needle guard further includes first and second arms extending substantially in the axial direction from the distal side of the base portion, with the first arm having a distal region and a proximal region. A distal wall is transversely arranged in the distal region of the first arm.

The needle guard also includes a stopping element which is arranged in the needle guard. The stopping element is made of a second material different from the first material and has a through-bore with a profile which is adapted to the principal outer profile of the needle shaft. In the case of e.g. circular cross-sections, a diameter of the through-bore can be slightly larger than a principal outer diameter of the needle. The stopping element may be formed by a washer integrally formed within the base portion.

In order to allow a trouble free movement of the needle relative to the needle guard when the needle is withdrawn from the catheter tube, the stopping element is preferably arranged such that its through-bore is in general alignment with the needle passage of the needle guard.

The stopping element can be a circular disk, a ring, or a washer. However, it need not necessarily be circular and can have any other geometric shape such as a rectangular square or triangular shape.

Preferably, the second material is of greater hardness and/or stiffness than the first material. For example, the first material could be a plastic material and the second material could consist of a metal, a ceramic or a rubber material, or any other type of material which is stiff and not as easily distorted as the first material.

The stopping element may be arranged within the base portion. Also formed from a different material, it can be integrated therein. As a preferred alternative, the stopping element may be arranged loosely on the needle between the two arms of the needle guard and floating on the needle shaft. In this embodiment, the stopping element may be formed by a tube-like element. It can be held by holding means, like a recess or protuberances in a predetermined section of the needle guard.

Needle guards of the above kind are used, for example, in catheter apparatuses. The invention therefore also provides a catheter apparatus including a needle guard in accordance with the present invention, with the catheter apparatus further including a catheter tube, a catheter hub and a needle having a needle shaft, a needle tip and a needle hub, wherein the needle shaft has a distal section and a proximal section, with at least the proximal section having a principal outer profile.

The needle also may have an enlargement provided between the distal section and the proximal section of the needle shaft. The enlargement has an outer profile one dimension of which is larger than a maximum dimension of the profile of the through bore of the stopping element. In a preferred embodiment, the enlargement is made by a crimping of the needle shaft. However, other ways of forming the enlargement are possible, such as applying additional material to the needle shaft, e.g. by soldering, welding or gluing etc.

The inner profile of the needle can either be reduced in the region of the enlargement, for example, if the enlargement is formed by crimping, or it can be substantially constant throughout the length of the needle, for example, if the enlargement is formed by applying additional material to the needle shaft.

The needle may also be formed with an opening arranged distally or proximally from the enlargement. This opening may be formed by a small slit which is cut into the needle shaft and which extends in axial direction for about a small distance, e.g. 0.3 to 1 mm. The opening is just large enough in order to provide an early blood flashback function close to the needle tip within the catheter tube such that the practitioner can recognize that he has placed the needle correctly within a patient's vein. In case of a correct positioning of the needle, blood pours out of the opening within the needle shaft into the space between the needle shaft and the inner wall of the transparent catheter tube and is visible to the practitioner.

Prior to the use of the catheter apparatus, the needle guard is arranged in the catheter hub near a proximal end of the needle shaft. In this situation, the needle extends completely through the needle guard, thereby deflecting the first arm of the needle guard outwards, i.e. at an angle to the axial direction, such that the distal wall of the first arm is supported on the needle shaft. Following the insertion of the catheter into a patient, the needle is withdrawn from the catheter tube and the needle shaft moves through the needle guard while the needle guard is retained in the catheter hub. Once the needle tip passes the transverse distal wall of the needle guard, i.e. such that the needle shaft no longer supports the distal wall, a restoring force ensures that the first arm of the needle guard is moved back into alignment with the axial direction of the needle guard, so that the needle tip is blocked by the distal wall of the needle guard, i.e. the needle tip is prevented from axially projecting out of the needle guard.

Once the needle tip is blocked by the distal wall and the needle is being further retracted, the enlargement of the needle shaft engages with the stopping element to prevent the needle guard from being removed from the needle shaft. The fact that the stopping element is made from a second material which is harder and less easily distorted than the first material of the base portion, has the effect that the needle guard is secured more effectively on the needle shaft and can be retained even if excessive external force is applied when pulling on the needle, as the enlargement is prevented from being pulled through the base portion of the needle guard due to the stopping element. Hence, it is prevented that the needle guard is removed from the needle tip accidentally and, as a result, the needle guard provides a better protection against accidental pricking and thus increased safety for the person handling the catheter apparatus.

In a further embodiment of the needle guard, a tension element surrounds the first and second arms of the needle guard. In the deflected state of the first arm, the tension element is expanded against a restoring force of the tension element. Once the needle shaft no longer supports the distal wall of the first arm, the tension element aids the repositioning of the first arm back into axial alignment with the axial direction. This repositioning is necessary so that the distal wall can block the needle tip from axially sliding out of the needle guard. In addition, the tension element helps to enclose a space between the first and second arms and thus helps to prevent the needle shaft and the needle tip from projecting sideways out of the needle guard. In other words, the tension element adds to the protective effect of the needle guard.

According to the invention, the two arms of the needle, in particular the first arm having the distal wall blocking the needle tip, do not have any recess in order to provide a high strength and a spring-like action of the first arm such that it is biased into the blocking position with its distal wall in front of the needle tip.

In a further embodiment of the needle guard, a groove is provided in a side of the distal wall, with the groove extending substantially in the axial direction. The groove acts as a guide groove for the needle shaft and aids the axial movement of the needle shaft relative to the needle guard. Moreover, the needle shaft is prevented from sliding sideways off the distal wall. Such a sideways movement would significantly increase the force required to move the needle shaft relative to the needle guard, which would prevent a correct functioning of the needle guard.

According to a further embodiment of the invention, the catheter hub within which the needle guard is received in a ready position, includes holding means for holding the needle guard even under retracting forces acting on the needle guard when the needle is retracted out of the patient's vein. These holding means may include a recess formed on the inner circumferential surface of the catheter hub into which a projection formed on the first arm of the needle guard securely engages in the ready position, i.e. when the first arm is deflected and spread apart from the second arm by the needle shaft. Alternatively, these holding means may include a bump formed on the inner circumferential surface of the catheter hub. The holding means on the inner circumferential surface of the catheter hub maybe also formed by a combination of a recess and a bump wherein the needle guard has a corresponding complimentary profile of a projection engaging the recess on the inner circumferential surface of the catheter hub and a recess engaging with the bump on the inner circumferential surface of the catheter hub. As an alternative, the holding means may include at least one outer arm formed on the base portion and adapted to engage the catheter hub on its outer circumferential surface. In particular the holding means may include two outer arms formed on substantially diametrical locations of the base portion and adapted to engage the catheter hub on its outer circumferential surface. By providing such holding means, the holding function is alternatively or additionally provided at the outside of the catheter hub. Thereby, the manufacturing effort can be reduced and the safety in operation may be further increased.

In a further embodiment, the catheter hub may have an opening or window in order to provide additional space for the deflected first arm in the ready position. The opening or window can be formed as a through-hole through the circumferential wall of the catheter hub. The opening in the circumferential wall of the catheter hub may also provide a holding edge acting as the holding means for holding the needle guard within the catheter hub in the ready position even under retracting forces applied on the needle by the practitioner.

Further advantageous embodiments of the invention and preferred apparatuses for
carrying out the invention are described in connection with the accompanying drawings.

BRIEF DESCRIPTION OF THE ACCOMPANYING DRAWINGS

The present invention will now be explained in more detail in the following with reference to preferred embodiments and to the accompanying drawings in which are shown.

DETAILED DESCRIPTION OF THE INVENTION

Figure 1:
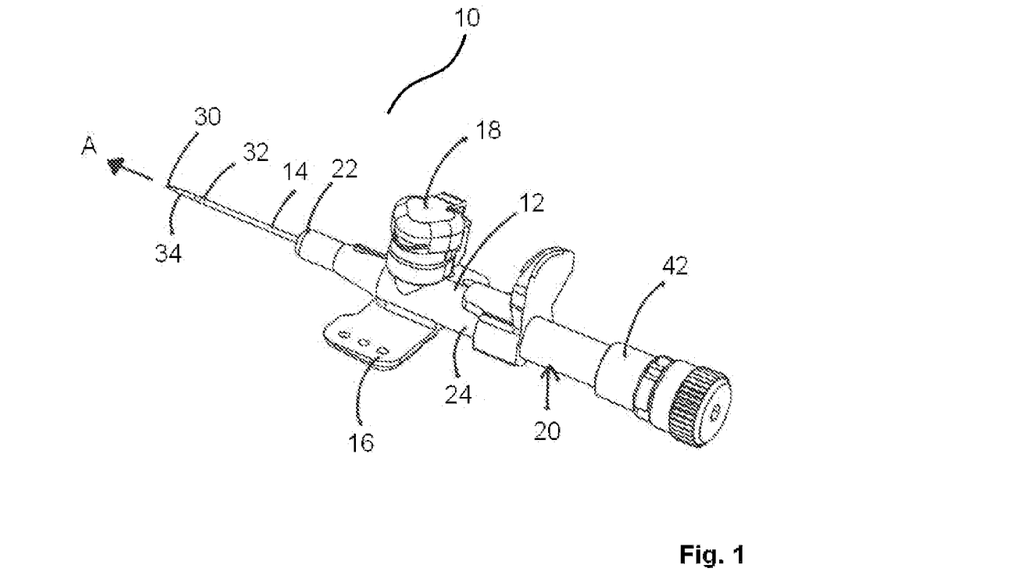
FIG. 1 illustrates a catheter apparatus in accordance with the present invention.

FIG. 1 shows a catheter apparatus 10 in accordance with the invention. The catheter apparatus 10 includes a catheter hub 12, a catheter tube 14, wings 16, a port 18 and a needle 20. The catheter hub 12 has a distal end 22 and a proximal end 24, the catheter tube 14 is arranged adjacent to the distal end 22 of the catheter hub 12.

Figure 2:
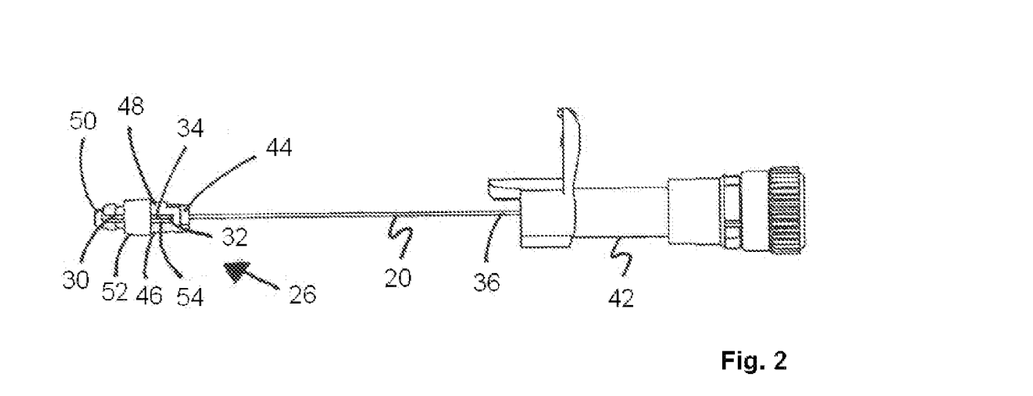
FIG. 2 illustrates a needle, needle hub and needle guard removed from the catheter apparatus of FIG. 1.

The needle 20, shown in FIG. 2, has a needle shaft 28, a needle tip 30 at a distal section 34 of the needle shaft and a needle hub 36 attached to a proximal end 36 of the needle shaft 28. Both, the distal section 34 and the proximal section 36 generally have the same outer profile. In the present embodiment, the distal and proximal sections 34, 36 have circular cross-sections with generally identical outer diameters.

An enlargement 32 of the needle 20 is provided between the distal section 34 and the proximal section 36 of the needle shaft 28. The enlargement 32 has a maximum dimension in a direction transverse to the needle shaft 28, which is greater than the outer diameter of the distal and proximal sections 34, 36. The enlargement 32 can be made, for example, by crimping the needle shaft 28.

Prior to use of the catheter apparatus 10, the needle 20 is received in the catheter hub 12 and the transparent catheter tube 14, such that the needle shaft 28 extends through the length of the transparent catheter tube 14.

A needle guard 26 is movably arranged on the needle shaft 28 and retained in the catheter hub 12 in the state prior to use of the catheter apparatus 10 (as shown in FIG. 1). The needle guard 26 has a base portion 44, a first arm 46, a second arm 48 and a distal wall 50. The distal wall 50 is arranged at a distal end of the first arm 46 and extends in a direction transverse to an axial direction A. A tension element or restrictor 52, for example, a silicone or rubber band or the like, surrounds the first and second arms 46, 48.

Upon withdrawal of the needle 20 from the catheter tube 14 and catheter hub 12 the needle shaft 28 moves relative to the needle guard 26, which is retained within the catheter hub 12, until the needle tip 30 is received in the needle guard 26. Once the needle tip 30 is received in the needle guard 26 the enlargement 32 of the needle shaft 28 engages with blocking means 38 provided in or close to the base portion 44 of the needle guard 26 such that the needle guard 26 can be pulled out of the catheter hub 12 together with the needle 20. An axial movement of the needle 20 relative to the needle guard 26 is now limited, as the distal wall 50 blocks the needle tip 30 and the engagement between the enlargement 32 and the base portion 44 of the needle guard 26 prevents the needle tip from being removed via the base portion 44, i.e. the needle tip 30 is safely surrounded by the needle guard 26, as is shown in FIG. 2.

FIGS. 3 to 6 show the needle guard 26 in more detail.

Figure 3A:
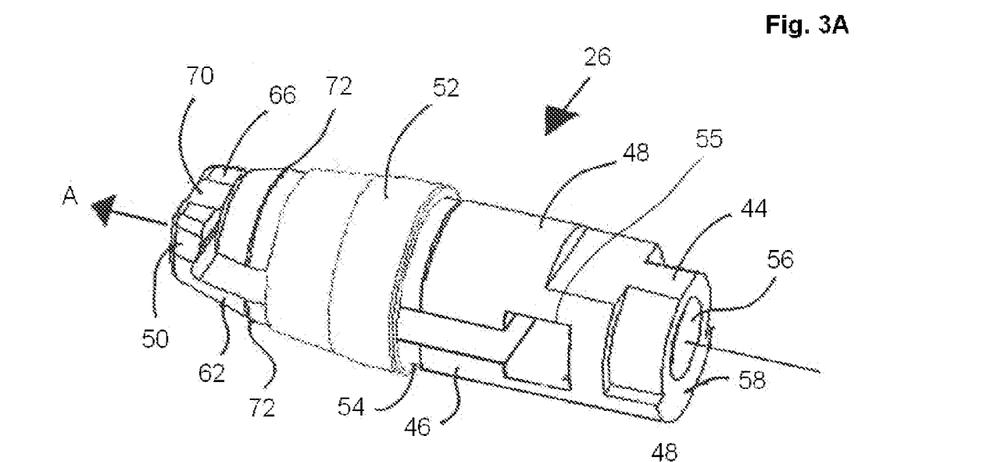
FIGS. 3A-3D illustrate the needle guard of FIG. 2.
Figure 3B:
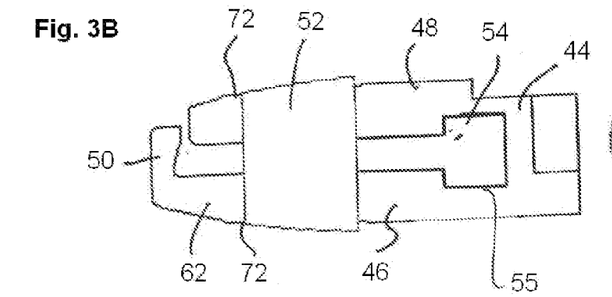
Figure 3C:
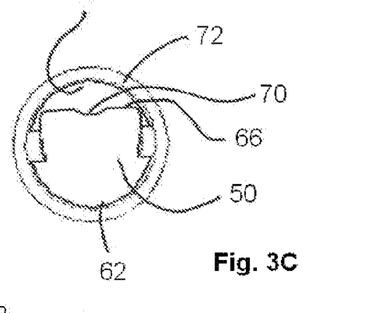
Figure 3D:
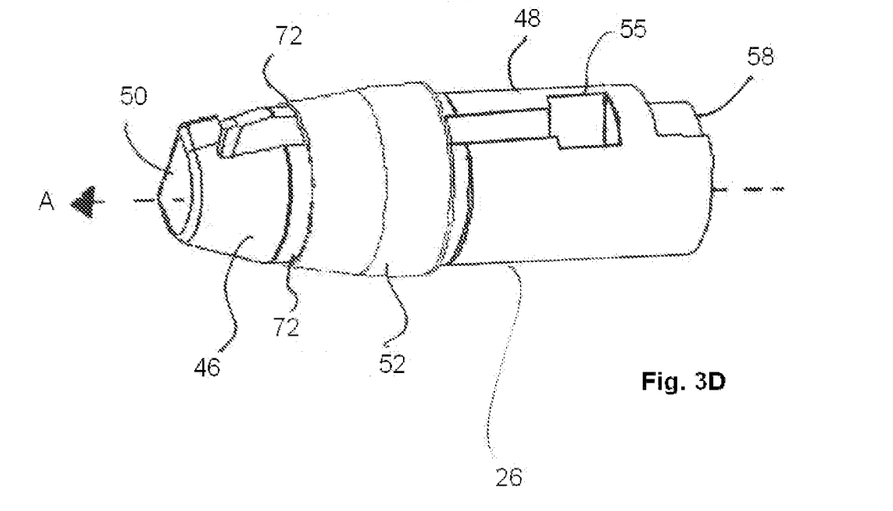

As can be seen from FIG. 3A, the base portion 44 has a needle passage 56 extending in the axial direction A from a proximal side 58 of the base portion 44 through the base portion 44 to a distal side 60 of the base portion 44. The needle passage 56 is configured to receive the proximal section 36 of the needle shaft 28 and allow movement of the needle shaft 28 relative to the needle guard 26. For this reason, the diameter of the needle passage 56 is slightly larger than the outer diameter of the proximal section 36 of the needle shaft 28.

Figure 4A:
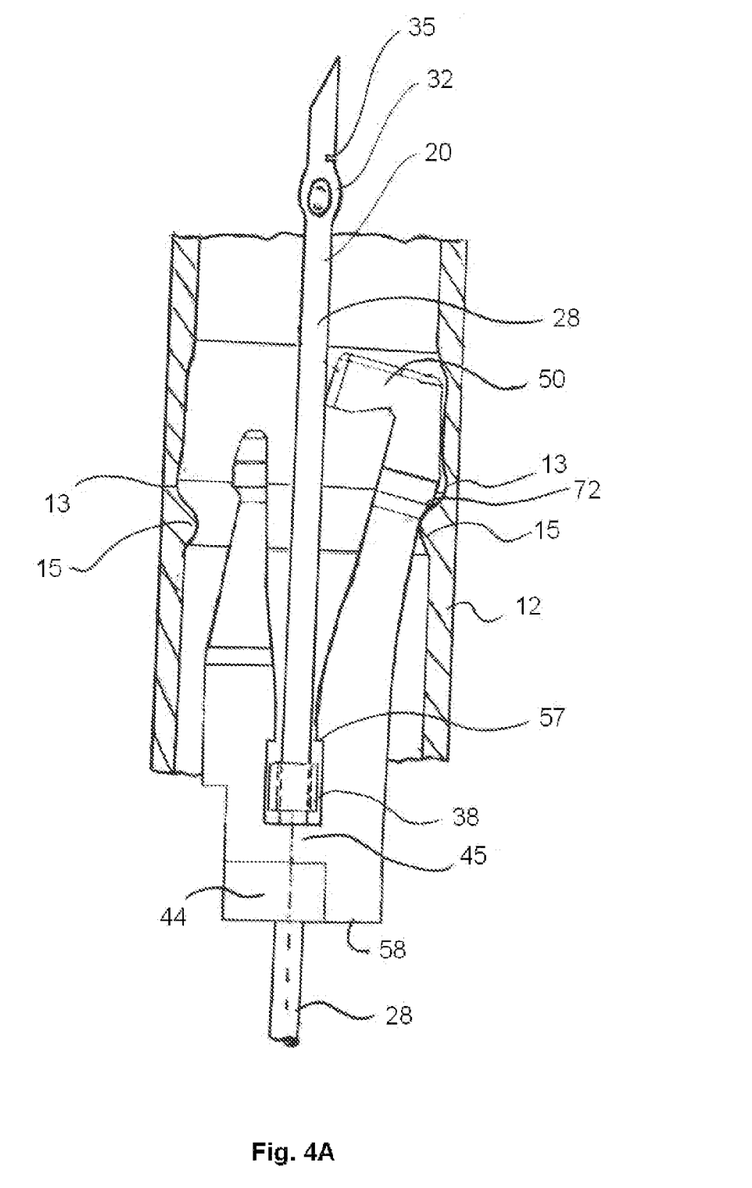
FIGS. 4A-4B are two illustrations illustrating the needle guard of FIG. 2 interacting with different kinds of catheter hubs wherein the tension element has been omitted for sake of clarity in the drawing.
Figure 4B:
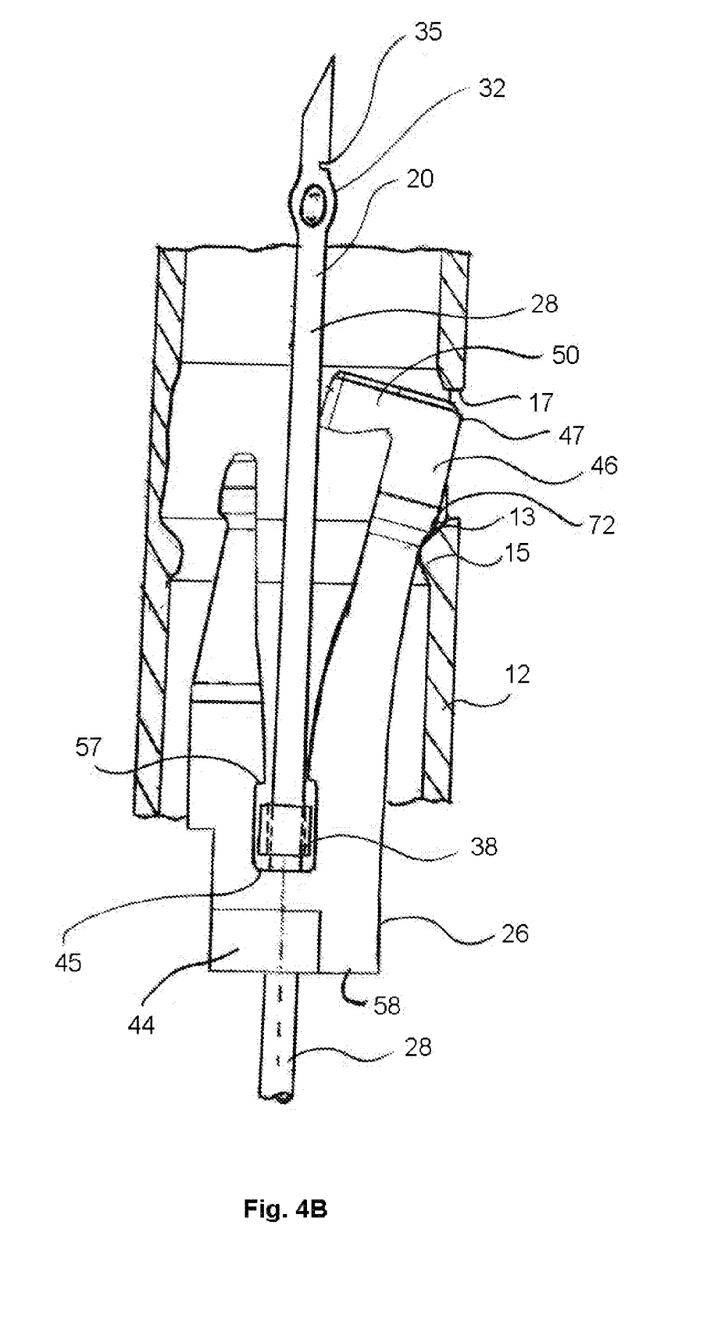
Figure 5:
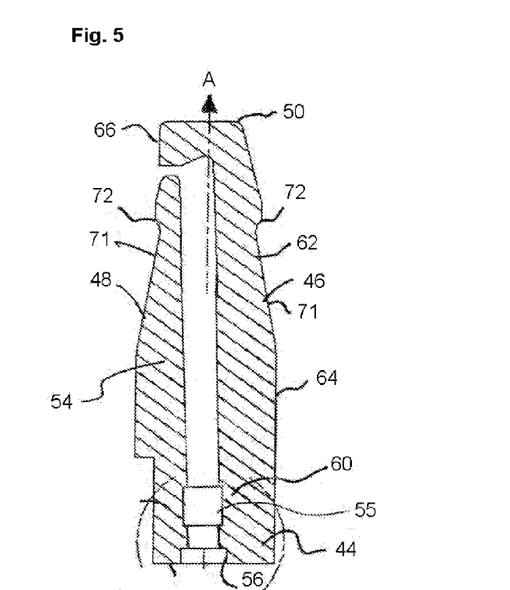
FIGS. 5 and 6 are sectional illustrations illustrating the needle guard of FIGS. 4.
Figure 6:
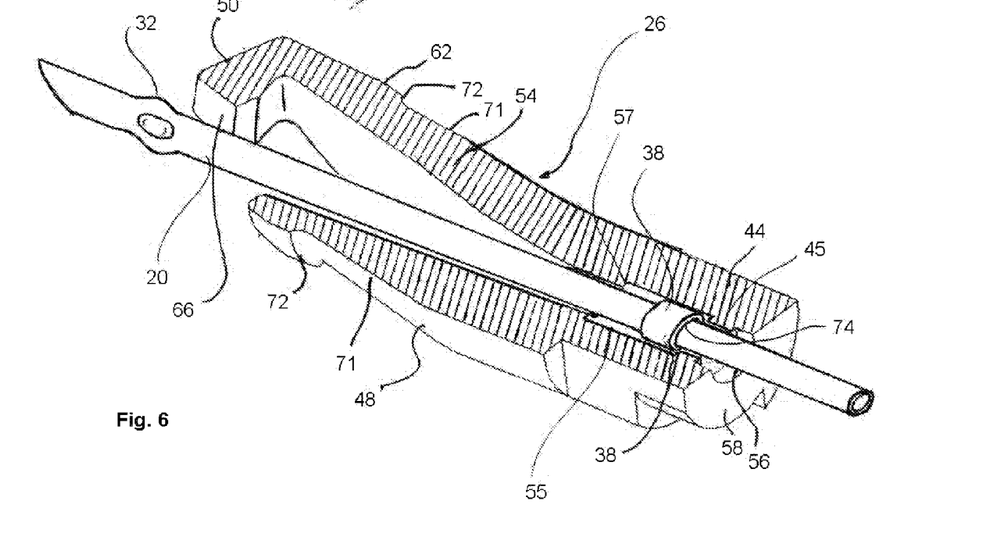

The first and second arms 46, 48 of the needle guard 26 extend generally in the axial direction A from the distal side 60 of the base portion 44, i.e. generally parallel to the needle shaft 28. The first arm 46 is formed without any recess on the outer side in order to provide a high biasing force in case it is deflected, as shown in FIG. 4A or 4B. The biasing force acts such the first arm 46 flexes back from a position as shown in FIGS. 4A and 4B to the relaxed position shown in FIGS. 3A to 3D.

The outer surfaces 71 of the distal regions 62 of the first and second arms 46, 48 generally taper from the base portion 44 towards the distal wall 50. At their distal ends, the tapered surfaces 71 are limited by protrusions or shoulders 72 formed on the first and second arms 46, 48. The shoulders 72 and the tapered surfaces 71 define the axial position of the tension element 52 and, in particular, prevent the tension element 52 from axially sliding off the first and second arms 46, 48.

The transverse distal wall 50 has a side 66 at its free end, in which a groove 70 is provided. The groove 70 extends in a direction generally parallel to the axial direction A and is used to guide the needle shaft 28.

FIGS. 3A to 3D show that close to the base portion 44, the needle guard has a internal recess 55. This internal recess 55 is provided for holding a floating tube like washer 38 (see FIGS. 4A, 4B), which is slidably movable on the needle shaft 20 and which has an outer diameter that is substantially larger than the opening 45 (see FIG. 6) in the base portion 44. The inner diameter of the floating washer 38 is substantially smaller than the largest diameter of the enlargement 32 close to the needle tip. The recess 55 is limited on its distal end by a shoulder 57. Hence, a collar 45 formed by the base portion 44 and the shoulder 57 provide movement limiting means for the floating washer 38. The floating washer 38 acts as a floating stopping means which prevents that the needle shaft 28 when he is completely retracted out of the needle guard 26.

As mentioned above, prior to the use of the catheter apparatus 10 the needle 20 extends through the catheter tube 14 and the needle guard 26 is arranged in the catheter hub 12. In this situation, the distal wall 50 of the needle guard 26 contacts the needle 20, with the needle shaft 28 being guided in the groove 70 in the side 66 of the distal wall 50. The needle shaft 28 thereby supports the distal wall 50, due to which the first arm 46 of the needle guard 26 is deflected outwards, i.e. away from the needle 20, against a restoring force of the tension element 52.

In order to retain the needle guard 26 in the catheter hub 12 while the needle 20 is being withdrawn from the catheter tube 14, the shoulders 72 provided on both the first arm 46 and the second arm 48 of the needle guard 26 engage with recesses 13 or protrusions 15 or combinations thereof (FIG. 4A) provided on the inner circumferential surface of the catheter hub 12. The protrusions 15 may form an annular ring extending along the entire inner periphery of the catheter hub 12, or they may form one or more ring segments extending along only a respective part of the inner periphery of the catheter hub 12. Similarly, the recesses 13 may form an annular groove extending along the entire inner periphery of the catheter hub 12, or they may form one or more groove segments extending along only a respective part of the inner periphery of the catheter hub 12.

As shown in FIG. 4B, the catheter hub 12 maybe also formed with a through-hole 17 forming a window which provides sufficient space for a distal radially outer portion 47 of the first arm 46 in the region of the distal wall 50 such that in the ready position shown in FIG. 4B the distal portion 47 may deflect to such an extent that it protrudes into the opening formed by the through-hole 17. The through-hole 17 additionally provides a holding function in order to prevent an axial movement of the needle guard 26.

Once the needle 20 has been withdrawn such that the needle tip 30 has passed the distal wall 50 and is received between the first and second arms, the needle shaft 28 no longer supports the distal wall 50. This causes the first arm 46 to reposition itself in axial alignment with the needle 20 due to the restoring force acting on the first arm 46 in its deflected state. The realignment of the first arm 46 is aided through the inherent biasing force of the first arm 46 and additionally through the use of the tension element 52. The realignment of the first arm 46 causes the shoulders 72 to disengage from the recesses or protrusions in the catheter hub 12 allowing the needle guard 26 covering the needle tip 30 to be removed from the catheter hub 12 together with the needle 20, with the guarded needle tip 30 being arranged in a space 54 which is bounded by the base portion 44, the first and second arms 46, 48, the distal wall 50 and the tension element 52.

The stopping element or stopper 38 is made of a material different to the material of the base portion 44, in particular, a material having a greater hardness and/or stiffness than the material of the base portion 44. Preferably, the stopping element 38 is made of metal or ceramic, but it can be made out of any other material which is stiff and is not easily bent.

The base portion 44 and first and second arms 46, 48 of the needle guard 26 can be made from a plastic material, for example by a moulding process.

As mentioned above, the stopping element 38 has a through-bore 74 which has a circular cross-section with its diameter being slightly larger than the principle diameter of the proximal section 36 of the needle shaft 28, in order to allow movement of the proximal section 36 of the needle shaft 28 relative to the stopping element 38. At the same time the diameter of the through-bore 74 is not only smaller than that of the needle passage 56 but also smaller than the maximum dimension of the enlargement 32 of the needle shaft 28, in order to prevent the enlargement 32 from passing through the through-bore 74.

Even in the event that an excessive external force is applied to the needle 20 and/or the needle guard 26, the stopping element 38 prevents the enlargement 32 of the needle shaft from being pulled through the needle passage 56 of the base portion 44. Thus, the stopping element 38 improves the safety of the needle guard 26.

Figures 7A, 7B, 7C:
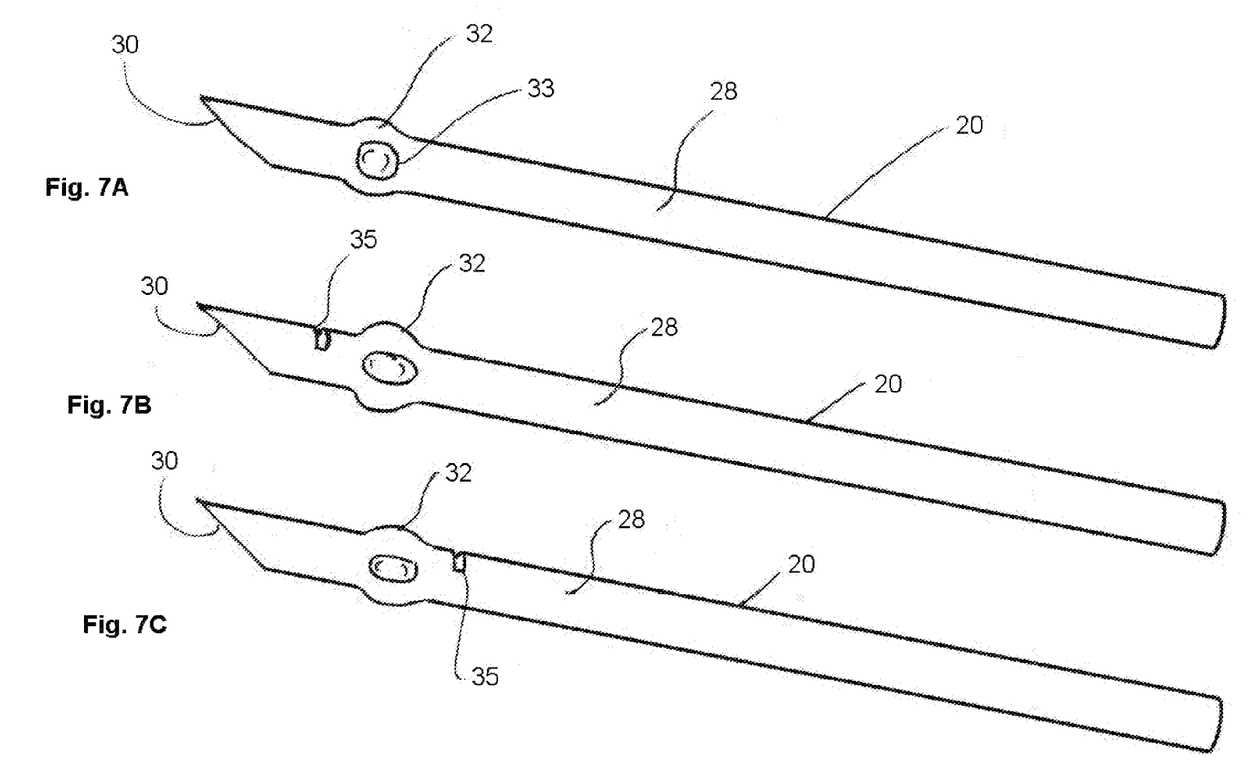
FIGS. 7A-7C illustrate different embodiment of needles.

FIG. 7A shows an embodiment of a needle 20 having a needle shaft 28, a needle tip 30 and an enlargement 32 formed by a crimp. The crimp is made by a local depression 33 such that lateral protrusions 32 result from the crimping process. The crimping process is controlled such that the internal cross-sectional area of the needle is not reduced substantially such that the through both laughed is not affected.

FIG. 7B shows the needle according to FIG. 7A, however having a slit 35 arranged slightly distally from the enlargement 32, such that it is still arranged within the catheter tube in the ready position. The slit 35 just extends over about 0.5 mm in axial direction and provides a through hole through the needle wall. Thereby, an early blood flashback within the transparent catheter tube 14 can be achieved when the needle is position into the patient's vein. Based on this blood flashback, the practitioner can see right after puncturing the patient whether the needle has been positioned correctly due to a small amount of patient's blood flooding the space between the needle shaft 28 and the transparent catheter tube 14.

FIG. 7C shows the needle according to FIG. 7B, however with the slit 35 arranged proximally from the enlargement 32. The slit 35 is dimensioned such that it does not affect the functioning of the needle guard 26.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, from the foregoing description, it will be apparent to one of ordinary skill in the art that many changes and modifications can be made thereto without departing from the spirit or scope of the invention as set forth herein.

Accordingly, it is not intended that the scope of the foregoing description be limited to the exact description set forth above, but rather that such description be construed as encompassing all of the features of patentable novelty that reside in the present invention, including all the features and embodiments that would be treated as equivalents thereof by those skilled in the relevant art. Thus, it is intended that the scope of the present invention herein disclosed should not be limited by the particular disclosed embodiments described above but should be determined only by a fair reading of the appended claims.

The invention claimed is:

1. An intravenous catheter apparatus, comprising:
a needle having a needle shaft, a needle tip at a distal end of the needle shaft and a needle hub mounted to a proximal end of the needle shaft,
an intravenous catheter tube mounted to a catheter huh and
a needle guard movable on the needle shaft,
wherein the needle guard comprises:
base portion having a needle passage extending in an axial direction from a proximal side of the base portion through the base portion to a distal side of the base portion,
first and second arms extending substantially in the axial direction from the distal side of the base portion and
a distal wall which is transversely arranged at a distal region of the first arm, wherein a recess provided in the needle guard receives a stopper structured to stop movement of the needle shaft relative to the needle guard, and
wherein the catheter hub provides an opening in order to provide space for the first arm while it is in a deflected state and the needle guard is in a ready position, wherein the opening is formed as a through-hole through a circumferential wall of the catheter hub.

2. The intravenous catheter apparatus according to claim 1, wherein the needle guard is made of a first material and wherein the stopper is made of a second material different from the first material.

3. The intravenous catheter apparatus according to claim 2, wherein the second material is of greater hardness and/or stiffness than the first material.

4. The intravenous catheter apparatus according to claim 1, wherein the needle shaft defines a principal outer profile and wherein the base portion has a through-bore with a profile which is adapted to the principal outer profile of the needle shaft.

5. The intravenous catheter apparatus according to claim 4, wherein the needle defines a principal outer diameter and wherein a diameter of the through-bore is slightly larger than the principal outer diameter of the needle.

6. The intravenous catheter apparatus according to claim 1, wherein the stopper is formed by a washer, a cylindrical tube body or a body having a polygonal cross-sectional shape.

7. The intravenous catheter apparatus according to claim 1, wherein the stopper defines a through-bore that is in substantial alignment with the needle passage of the needle guard.

8. The intravenous catheter apparatus according to claim 1, wherein the stopper is arranged loosely on the needle between the two arms of the needle guard and is floating in the recess of the needle guard on the needle shaft.

9. The intravenous catheter apparatus according to claim 1, wherein the needle shaft is structured to allow limited movement of the stopper along the length of the needle shaft.

10. The intravenous catheter apparatus according to claim 1, wherein the needle shaft defines a distal section and a proximal section and wherein the needle has an enlargement provided between the distal section and the proximal section of the needle shaft.

11. The intravenous catheter apparatus according to claim 10, wherein the stopper defines a through-bore defining a profile and wherein the enlargement has an outer profile in one dimension of which is larger than a maximum dimension of the profile of the through-bore of the stopper.

12. The intravenous catheter apparatus according to claim 10, wherein the enlargement is made by a crimping of the needle shaft.

13. The intravenous catheter apparatus according to claim 1, wherein the needle is formed with an opening dose to the needle tip, wherein the opening of the needle is located within the catheter tube when the needle guard is in the ready position.

14. The intravenous catheter apparatus according to claim 1, wherein the needle shaft defines a distal section and a proximal section, wherein the needle has an enlargement provided between the distal section and the proximal section of the needle shaft and the needle has a slit, and wherein the slit is arranged distally or proximally from the enlargement.

15. The intravenous catheter apparatus according to claim 14, wherein the slit extends in the axial direction for a distance of 0.3 to 1 mm.

16. The intravenous catheter apparatus according to claim 1, further including a restrictor structured to apply a tensioning force to the first and second arms of the needle guard.

17. The intravenous catheter apparatus according to claim 16, wherein the restrictor at least partially surrounds the first and second arms of the needle guard.

18. The intravenous catheter apparatus according to claim 16, wherein the restrictor helps to enclose a space between the first and second arms.

19. The intravenous catheter apparatus according to claim 1, wherein the needle guard provides a guide groove in a side of the distal wall, the groove extending substantially in the axial direction.

20. The intravenous catheter apparatus according to claim 1, wherein the catheter huh defines an inner circumferential surface that is structured to hold the needle guard against retracting forces.

21. The intravenous catheter apparatus according to claim 1, wherein the catheter hub defines an inner circumferential surface and further comprises a recess or a bump formed on the inner circumferential surface of the catheter hub adapted to engage a projection or recess formed on the first arm of the needle guard.

22. The intravenous catheter apparatus according to claim 1, wherein the catheter hub defines an outer circumferential surface and wherein the base portion is structured to engage the catheter hub on the outer circumferential surface.

23. The intravenous catheter apparatus according to claim 1, wherein the opening is structured to receive at least a portion of a distal outer portion of the first arm to restrict axial movement of the needle guard.

* * * * *

UNITED STATES PATENT AND TRADEMARK OFFICE
CERTIFICATE OF CORRECTION

PATENT NO. : 9,636,484 B2
APPLICATION NO. : 14/380358
DATED : May 2, 2017
INVENTOR(S) : Rishi Baid It is certified that error appears in the above-identified patent and that said Letters Patent is hereby corrected as shown below:

In the Claims

1) In Claim 1, Line 24 of the issued patent, replace the word "huh" with the word "hub";

2) In Claim 1, Line 28 of the issued patent, add the word "a" before the words "base portion having a needle passage"; and 3) In Claim 13, Line 22 of the issued patent, replace the word "dose" with the word "close".

Signed and Sealed this
First Day of August, 2017

Joseph Matal
*Performing the Functions and Duties of the*
*Under Secretary of Commerce for Intellectual Property and*
*Director of the United States Patent and Trademark Office*